United States Patent [19]

Granier

[11] 4,202,346
[45] May 13, 1980

[54] CATHETER FOR THE EXAMINATION OR TREATMENT OF A BLOOD VESSEL AND APPARATUS FOR THE UTILIZATION OF THIS CATHETER

[75] Inventor: Pierre M. Granier, Nogent-sur-Marne, France

[73] Assignee: Societe d'Etudes et d'Applications Technologiques-Serat, Geneve, France

[21] Appl. No.: 822,942

[22] Filed: Aug. 8, 1977

[30] Foreign Application Priority Data

Aug. 10, 1976 [FR] France ............................ 76 24403

[51] Int. Cl.$^2$ ............................................. A61B 6/00
[52] U.S. Cl. .................................. 128/658; 128/325; 128/349 B
[58] Field of Search .............. 128/348, 349 R, 349 B, 128/349 BV, 350, 351, 214 R, 214.4, 325, 218 A, 2 A, 214 F, DIG. 16, DIG. 9

[56] References Cited

U.S. PATENT DOCUMENTS

| | | | |
|---|---|---|---|
| 3,834,394 | 9/1974 | Hunter et al. | 128/325 |
| 3,888,239 | 6/1975 | Rubinstein | 128/2 A |
| 3,978,863 | 9/1976 | Fettel | 128/DIG. 16 X |
| 3,983,864 | 10/1976 | Sielaff et al. | 128/214.4 X |
| 4,044,757 | 8/1977 | McWhorter et al. | 128/218 PA X |
| 4,085,757 | 4/1978 | Pevsner | 128/348 X |

Primary Examiner—Stephen C. Pellegrino
Attorney, Agent, or Firm—Schuyler, Birch, McKie & Beckett

[57] ABSTRACT

This catheter comprises at least one tube and preferably two tubes. These tubes are, at one of their ends, parallel and open out into an inflatable balloon and are, at their opposite ends, independent and extend through an end member and terminate beyond the end member in a flared end portion. The latter is clamped in a sealed manner between the end member and a cylindrical socket. The latter is adaptable in a receiving head of an apparatus which is integral with a syringe or other source of fluid so that the tube is thus supplied with safety with fluid such as a contrasting product, a product which is opaque to X-rays or a silicone for obturating the vessel for the purpose of inflation or delfation of the balloon, for the control of its position and possibly for the definitive obturation of the vessel. This catheter and the apparatus are also particularly adaptable for neuroradiological examinations and to treatments of blood vessels.

20 Claims, 9 Drawing Figures

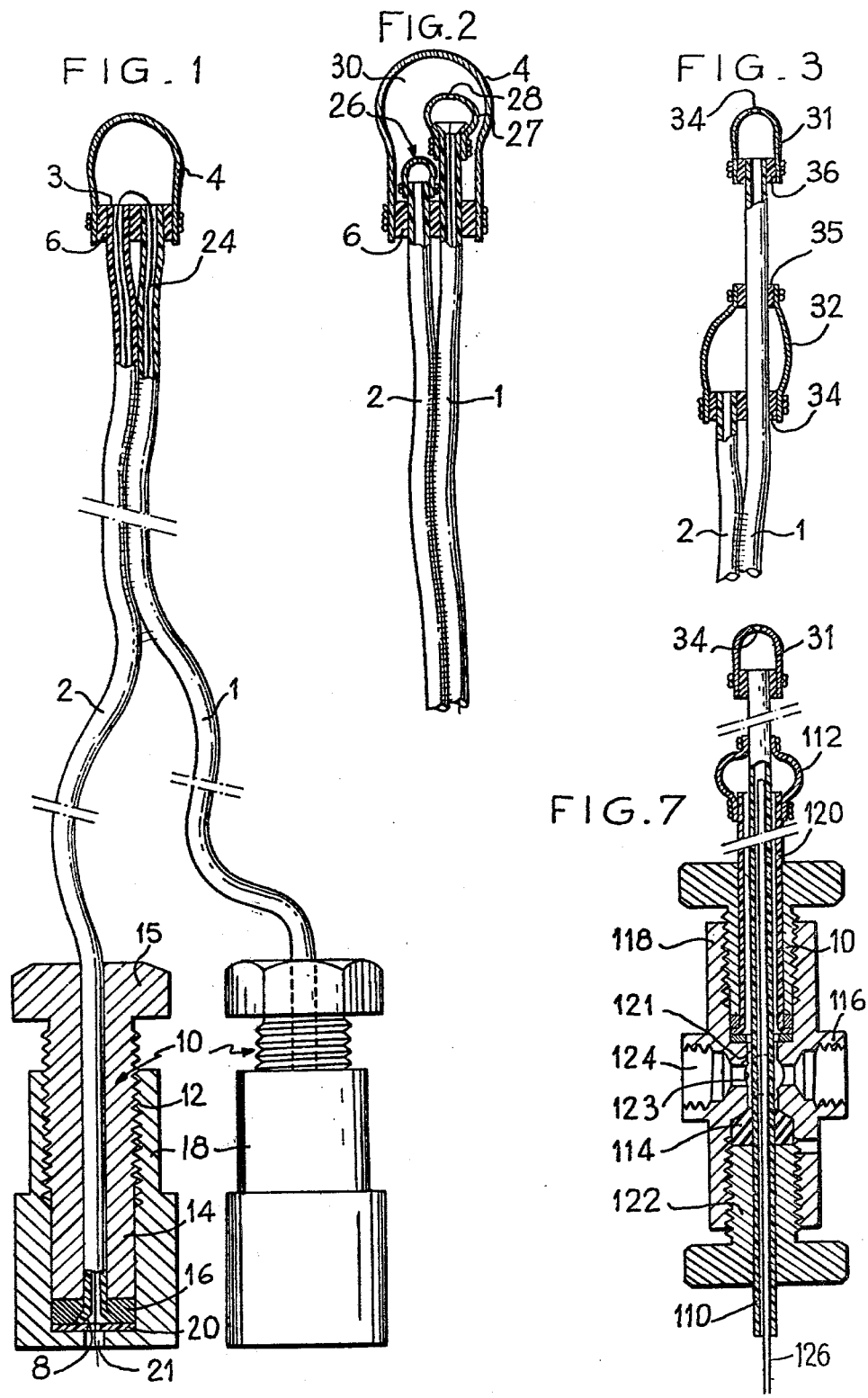

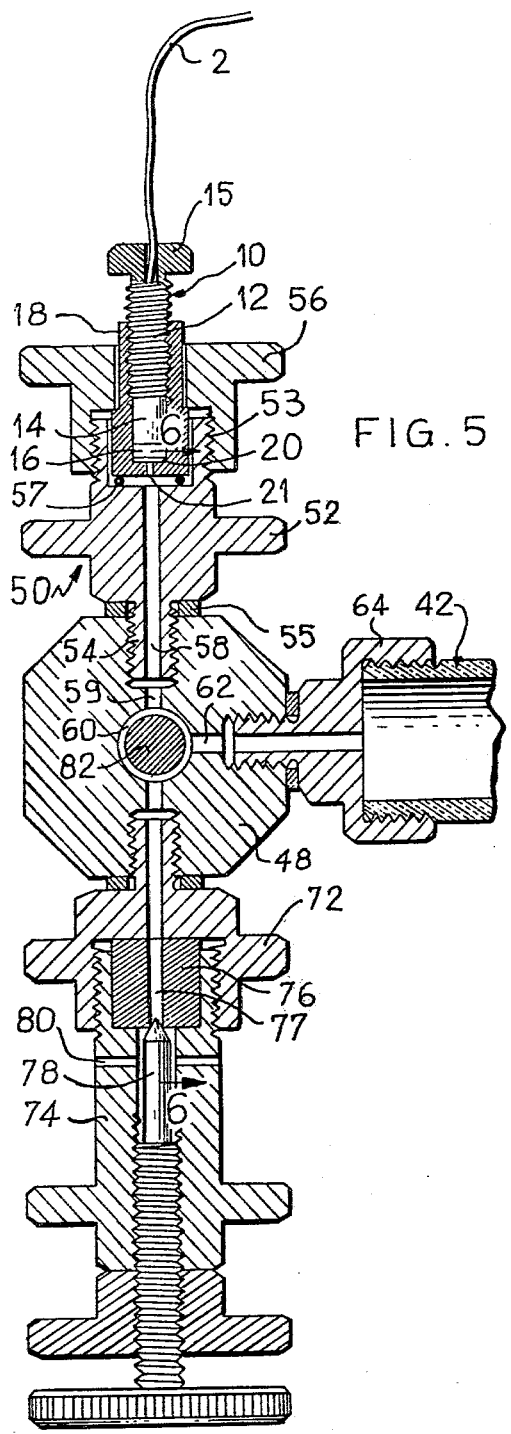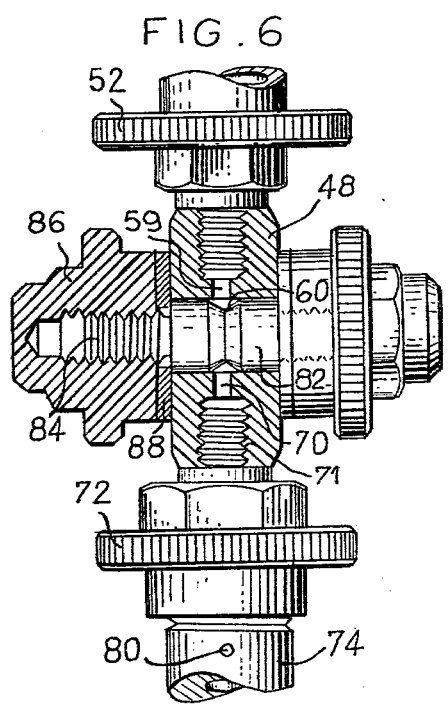

FIG_8
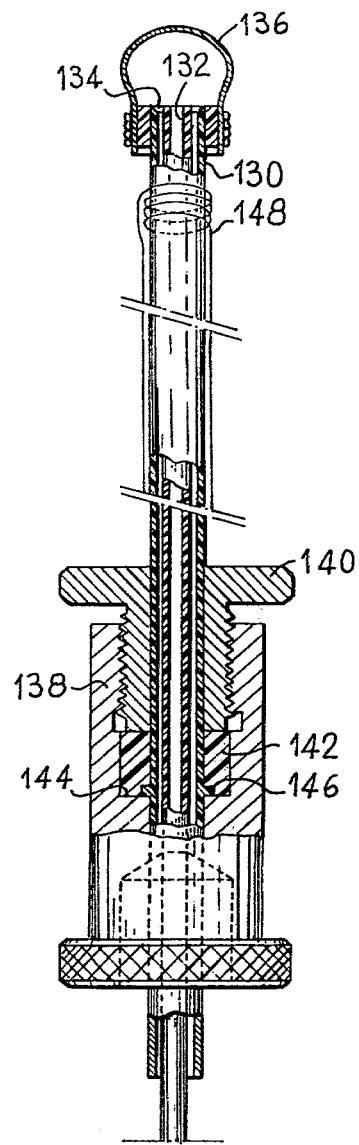
FIG_9
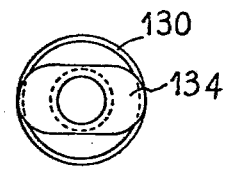

CATHETER FOR THE EXAMINATION OR TREATMENT OF A BLOOD VESSEL AND APPARATUS FOR THE UTILIZATION OF THIS CATHETER

The examination and the obturation of blood vessels by means of a small inflated balloon have been envisaged many years ago. Some patients have been treated by these means, which have permitted the avoidance of serious surgical operations such as trepanning. Examinations have also been facilitated. However, this technique has not been generalized up to the present time, owing to difficulties encountered in achieving, in succession, the introduction, the inflation and deflation and even possibly the leaving of the balloon in position, in an absolutely reliable and precise manner. It is indeed necessary to secure the balloon to a catheter or probe so as to be able to inflate it or deflate it at exactly the desired moment and to have means for releasing it so as to withdraw the catheter without danger of this separation between the balloon and catheter occurring prematurely, which would be extremely dangerous for the patient.

An object of the present invention is to solve this problem by providing a catheter which permits a reliable supervision of the displacement of the balloon in the vessels and the inflation or deflation thereof whenever necessary and which can even be withdrawn either alone or accompanied by the balloon.

According to the invention, there is provided a catheter comprising at least one tube which opens at one end thereof into an inflatable balloon and which is clamped at the other end thereof in a sealed manner between an end member mounted thereon and an outer connection socket.

Preferably, the catheter comprises a plurality of tubes which are parallel and interconnected at the end of the tubes in the vicinity of the balloon and are independent at the opposite end thereof.

The tubes may be formed in one piece by moulding or manufactured independently and welded together or mounted coaxially.

Before use, each tube is connected, through an orifice in the socket, to a source of fluid such as a contrasting product opaque to X-rays or a viscous rapidly solidified product, for example silicone. The first fluid introduced, usually the contrasting product, expels the air and thereafter allows the guiding of the balloon of the catheter to the point to be treated by inflation and deflation. The product thereafter introduced urges back and replaces this fluid. When this product is viscous, it may, owing to its rapid solidification, constitute an element for obturating the vessel. No risk of penetration of air or other product between the socket and the catheter is to feared and the socket can be easily adapted to a receiving head and supported in a strictly sealed manner, which ensures high safety of operation. This socket is moreover easily removable.

According to a first embodiment, all the tubes open into the same balloon.

According to another embodiment, the tubes each open into a separate balloon, one of these tubes extending throughout the balloon of the other. Thus one of the balloons serves to guide the displacement of the catheter and acts as a check-valve in the vessel, whereas the other permits the treatment.

In a modification, the balloon may be provided with an orifice permitting a treatment by suction or, on the contrary, by injection of the product in the vessel, and possibly a direct obturation of the latter, the balloon being thereafter withdrawn with the catheter.

The invention also relates to an apparatus for examining or treating a blood vessel by means of such a catheter, which comprises, on a fixed support, at least two syringes one of which syringes contains a fluid product and the other a viscous product, each of which syringes being controlled by a micrometer screw and each being integral with a receiving head for receiving the catheter connecting socket, means for a sealed clamping of the socket in the head and evacuating air, a hypodermic needle for introducing the catheter in the vessel of the patient and means for supplying treating product to the passageway between the needle and the catheter.

The syringes are controlled with precision by the micrometer screw which ensures, in turn, the supply of product to the catheter, each removable socket being capable of being connected to a syringe and the clamping means and means for evacuating air ensuring a complete absence of undesirable air. Likewise, prior or simultaneous treatments may be carried out automatically with the same needle. The apparatus therefore permits the penetration of the balloon in a blood vessel, the supervision of its progression, the inflation and deflation of the balloon whenever this is required at precise regions and even, possibly, the abandonment thereof for effecting neuroradiological examinations or treatments in the vessel itself or in a neighbouring place.

The following description of one embodiment, given merely by way of example and shown in the accompanying drawings, will bring out the advantages and features of the invention.

In the drawings:

FIG. 1 is a plan view, with parts cut away, of a catheter according to the invention;

FIG. 2 is a partial view of a catheter in a modification;

FIG. 3 is a view similar to FIG. 2 of another modification;

FIG. 5 is a sectional view, to an enlarged scale, of the connection of the catheter;

FIG. 6 is a sectional view, taken on line 6—6, of FIG. 5;

FIG. 7 is a partial view of a catheter according to another modification;

FIG. 8 is a partial view of another modification of the catheter, and

FIG. 9 is an end elevational view, to an enlarged scale, of the two tubes of the catheter shown in FIG. 8 before the mounting of the balloon.

Figure 4:
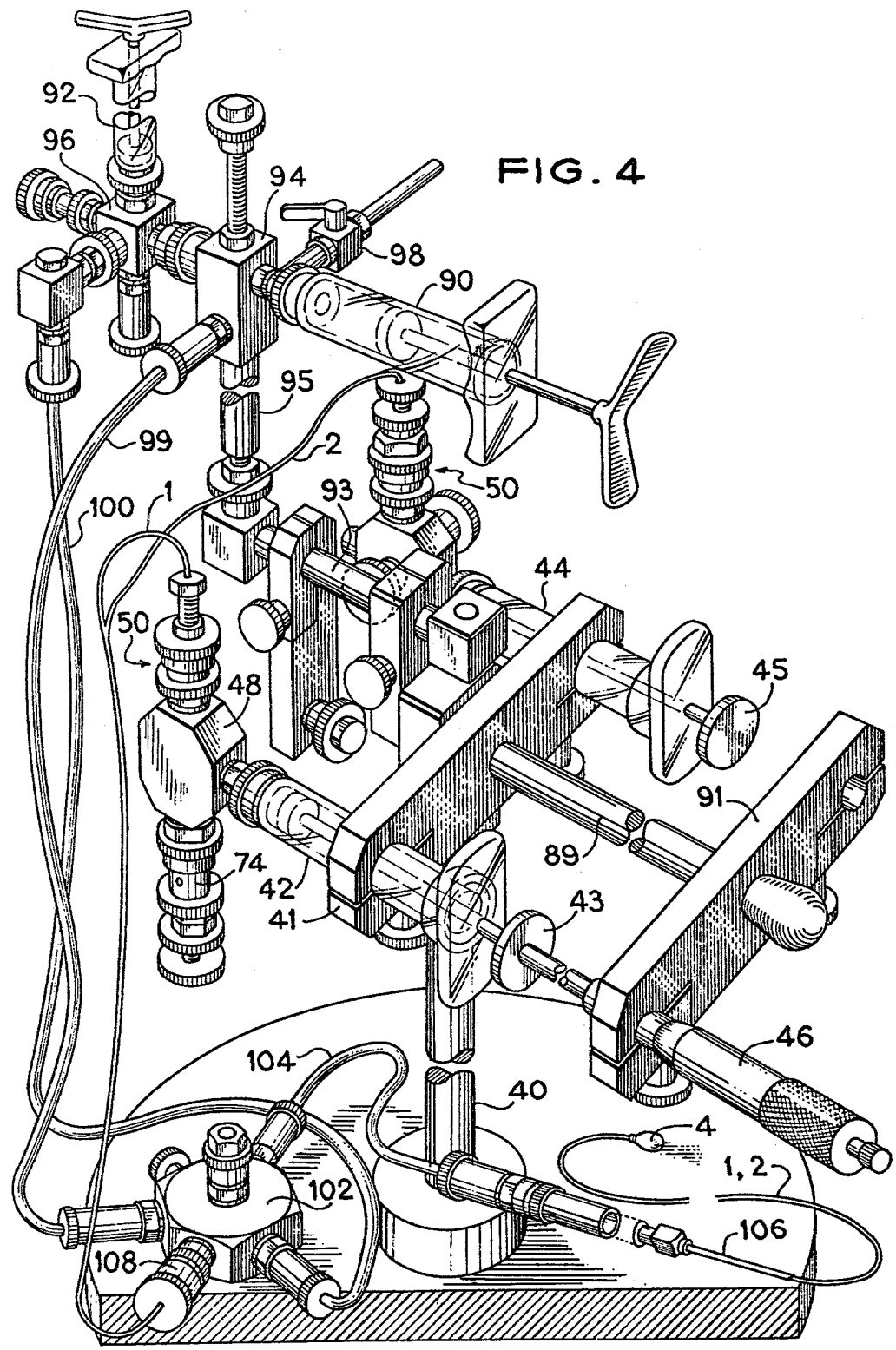
FIG. 4 is a perspective view of an apparatus according to the invention.

As shown in FIGS. 1 and 2, the catheter comprises at least one capillary tube and two in the illustrated embodiments which are made from a plastics material compatible with the requirements of medicine. These tubes 1 and 2 are integral with each other, in the vicinity of one of the ends 3 thereof, but are independent from each other at the opposite end 8. They are preferably obtained by moulding and are in a single piece but they may also be manufactured separately and welded together in a part of the length thereof. The attached ends of the tubes 1 and 2 are fixed by means of an annular ring 6 or by like means, to a small balloon 4 of latex or any other expansible material. The independent ends 8 of the tubes 1 and 2 each support a screwthreaded end member 10 provided with an axial bore and mounted on the tube. This end member 10 comprises a body 12 which has an external screwthread and is extended at one end by a tubular portion 14 and is provided at the other end with a handling head 15. A washer 16 is also mounted on the tube 2 or the tubular portion 14 and the end 8 which is preferably flared in the shape of a truncated cone so that its outside diameter exceeds the inside diameters of the washer 16 and end member 10 and prevents the separation of these members and the corresponding tube.

The end member 10 is screwed inside a socket 16 (FIG. 5) which is provided with an internal screwthread and closed at the end thereof opposed to the screwthread by an end wall 20 provided with an orifice 21 whose diameter is substantially equal to the diameter of the tube of the catheter. A washer 22, interposed between the end wall 20 and the tube 8, ensures a fluid-tight contact between these different parts. This washer is preferably of polytetrafluorethylene or the like, so that it is not attacked by the products flowing in the catheter.

The socket 18 is thus assembled in a fluidtight manner with the end member 10 and the corresponding tube and can be shifted with the latter. This socket has a substantially cylindrical outer shape and can easily be mounted in a supply head 50 (FIG. 4) connected to a syringe or any other suitable source of fluid or separated from this head. Thus, the tube 1 and/or tube 2 can supply different fluids to the balloon in turn as they are connected in advance to the sources of fluid, which eliminates any risk of introduction of air, or can even be shifted from one head to the other. For example, in the course of a treatment in a blood vessel, one of the tubes 1 is connected to a source of contrasting product which fills the balloon 4 while expelling the air by way of the tube and permits supervising it by, for example, radioscopy in the course of its progression in the vessels of the patient. This tube is thereafter shifted and connected to a source of viscous product opaque to X-rays, which, when it enters the catheter, expels the contrasting product and inflates the balloon. Preferably, a silicone or like product which solidifies very rapidly is employed for this purpose so that the balloon 4 is not only inflated but is rendered solid and can ensure an effective obturation of the vessel to be treated. The catheter is then withdrawn whereas the balloon remains in position.

For this purpose the catheter shown in FIG. 1 comprises, for example, inside the tubes 2 and 1 a removable flexible axial filament or thread-like member of plastics or metallic material which is unaltered by the fluid product or by the viscous product but which may be easily dissolved by introduction of an appropriate chemical product after solidification of the product. The destruction or removal of the filament 24 of one of the tubes 1 and 2 creates in the centre of the solidified silicone which fills this tube a conduit through which may pass a chemical product which dissolves the wall of the balloon, ultrasounds forming a wave antinode which breaks the fastening of this balloon, an electric resistance whereby it is possible to melt the catheter, or any like means capable of destroying the ring 6 and detaching the balloon. This means is of course inert with respect to the solidified viscous product which retains the dimension required for the obturation of the vessel but is no longer attached to the tubes 1 and 2. The catheter can then be withdrawn with safety, the balloon remaining in position in the chosen position.

According to a modification shown in FIG. 2, the ring 6 maintains at the same time as the main balloon 4 a flexible diaphragm 26 of a material similar to that of the balloon which terminates one of the tubes, namely the tube 2 in FIG. 2. The tube 1 thus opens into the chamber 30 defined between the diaphragm 26 and the balloon 4. The end thereof may be free, but it is preferably provided with a balloon 27 which is provided with a small orifice in the centre part thereof. The diaphragm 26 thus performs the function of a check-valve when the silicone is introduced by way of the tube 1. The silicone fills the chamber 30 very gradually as a function of the dimension of the orifice 28 and is solidified in this chamber which inflates but has a volume which may be closely controlled. When the obturation is sufficient, a chemical product entering by way of the tube 2 detaches both the balloons 4 and 27 and the diaphragm 26 and thereby permits the abandonment of the obturating product in the vessel and the withdrawal of the catheter without the balloon.

In some cases it may be preferable to eliminate the operation of the separation of the balloon. A catheter is then employed which comprises a tube 1 connected by a ring 36, similar to the ring 6 for fixing the balloon 4, to a balloon 31 which is provided with a small orifice 34 which is carefully calibrated in accordance with the desired rate of flow of the silicone. This orifice may be free as shown in FIG. 3 or provided with a nozzle, for example of glass, which imparts thereto a precise and constant dimension. The silicone or other viscous product is then solidified directly in, and oturates, the vessel. A catheter of this type also permits an injection of a metered amount of a treating product or a localized drawing off of the contents of the vessel.

A tube 2 is preferably associated with the tube 1 and opens into a second small balloon 32 which is formed by a flexible wall fixed, on one hand, to a ring 33 mounted on the end of the tube 2 and through which the tube 1 extends, and, on the other hand, on a ring 35 through which the tube 1 also extends. The tube 1 therefore extends completely through the balloon 32. The balloon receives the contrasting product and may be inflated and deflated as required to facilitate the supervision of the position of the catheter or for forming a check-valve in the vessel. The perforated balloon 31 serves as a metering or dosing means for the obturating silicone which consequently arrives very slowly in the vessel of the patient and is solidified progressively and obturates the desired passageways irrespective of the dimension of these passageways which may even be large with respect to the size of the inflated balloon. This balloon 32 is thereafter deflated to permit the withdrawal of the catheter. The free end of the tubes of this catheter are provided, as the ends of the catheter shown in FIG. 1, with end members 10 mounted in sockets 18 for assembly with a fluid distributing head.

To reduce the overall size of the catheter, it may be advantageous to mount the tubes one inside the other. The catheter then has two coaxial tubes 110 and 120 (FIG. 7). The tube 120 carries, at one end thereof, a balloon 112 which is similar to the balloon 102 and has also extending therethrough the tube 110 which is coaxial and, at the other end thereof, an end member 10 beyond which the tube 110 extends. This end member 10 is screwed in a socket 118 which is integral with a body 116 provided with an axial bore 121 for the passage of the tube 110 which is closed in a sealed manner by an elastically yieldable plug 114, for example of silicone, which is clamped against the tube 110 by a stuffing box gland 122. The passage 121 extends through a central cavity 123 into which at least one cavity 124 opens for receiving a syringe or other source of fluid (not shown) adapted to supply product to the tube 120 and the balloon. Beyond this cavity 123, the tube 110 extends through and beyond the gland 122 where it is integral with an end member 10 and a socket 18 similar to those shown in FIG. 1. The elasticity of the plug 114 is such that not only it ensures the sealed closure of the lower part of the cavity 123 around the tube 110, but this tube 110 itself may be closed by a suitable tightening of the gland.

The tube 110 may terminate in a small pierced balloon 31 as shown in FIG. 7 or by a closed balloon similar to the balloon 4 of FIG. 1. It may also be calibrated so as to have merely a capillary orifice and be devoid of a balloon, the balloon 112 of the tube 120 acting alone. In the latter case, the positioning of the catheter may be guided by a metallic probe 126 which is previously introduced in the vessels of the patient and on which the tube 110 is mounted. The whole of the catheter is then driven along this probe until the desired place is reached. The probe 126 can then be withdrawn and the catheter connected to a source of fluid.

According to another modification shown in FIGS. 8 and 9, two coaxial tubes 130, 132 of substantially the same length are freely mounted one inside the other. The axial displacement of the inner tube 132 is however limited by two diametrically opposed tabs 124 which are disposed at the end thereof and bear against the edge of the outer tube 130. A small balloon 136 is secured to the tube 130 in the same way as the balloon 4.

At the end opposed to the balloon 136, the tube 130 extends through an end member 140 and a socket 138 which is screwed on the end member. The socket 138 contains an annular ring 142 of an elastically yieldable material, such as rubber, which is blocked against an inner shoulder 144 of the socket 138 so that the tightening of the end member 140 presses it against the tube 130 and causes the latter to approach the inner tube 132. When the tightening is sufficient, the two tubes come into contact and the tube 130 is closed. The tube 130 is extended however to outside the socket 138 around the tube 132 and thus puts the balloon 136 in communication with the atmosphere. The tube 132 is integral with an end member 10 and with a connecting socket 18 which permit the desired injections in the balloon 136. Preferably, a flange 146 integral with the tube 130 is clamped between the ring 142 and the shoulder 144 and holds the socket axially stationary with respect to this tube.

In the embodiment shown in FIG. 8, the catheter is also provided with an elastically conductive filament or wire which is insulated and wound around the tube 130 of the balloon 136 and connected to a source of electricity. When it carries current, this wire or filament melts the tubes 130 and 132 and releases the balloon 136 which may be abandoned in the treated vessel, whereas the catheter is withdrawn.

Whatever be the chosen embodiment, the catheter is preferably employed with an apparatus such as that shown in FIG. 4 which comprises a support 40 on which there are mounted by clamps 41 at least two syringes 42 and 44 each of which is controlled by a micrometer screw 46 only one of which has been shown in order to simplify the drawing.

Each of the syringes 42, 44 communicates with a distributing element 48 on which is mounted a supply head 50. This head comprises a cylindrical end member 52 (FIG. 5) having an external screwthread 53 and provided with an axial bore 58 and extended by a hollow screwthreaded rod 54 for fixing to the distributing element 48, a washer 55 ensuring the seal. The inner cavity of the end member has an inside diameter larger than the outside diameter of the socket 18. The latter is therefore introduced with clearance and maintained in position by means of a cap 56 which is mounted freely thereon but is screwed on the screwthread 53 of the end member 52. The seal between the socket 18 and the end member 52 is ensured by an annular sealing element 57 which bears against the end of the cavity of the end member and is crushed by the socket 18 when the cap is tightened so as to render the communication between the conduit 58, the orifice 21 and the catheter 2 fluid-tight. However, this sealing element permits a bleeding of the conduit 58 and of the cavity of the end member 52 since it may be untightened at will by a slight unscrewing of the cap 56 and thus permit the escape of air urged back by the product coming from the syringe 42 which filled the conduit 58 of the end member 52 before the injections in the catheter.

The inner bore 58 of the rod 54 is thus in the extension of the orifice 21 of the socket 18 and the tube of the catheter. Inside the distributing element 48, this bore 28 communicates with a conduit 59 and a central cavity 60 with which communicates at least one conduit 62. Moreover, the distributing element 48 supports at least one second end member 64 which is screwed thereon in the same manner as the end member 52 and in which there is mounted the body of a syringe 42 for example. The cavity 60 thus puts the supply syringe in communication with the tube of the catheter 2 or 1.

At least that one of the distributing elements 48 which is associated with the syringe 42 is also provided with a third conduit 70 and supports an end member which is provided with an axial bore 71 and has an internal screwthread and in which there is screwed the body 74 of a bleeding device which permits in particular the deflation of the balloon. A ring of teflon (trademark) 76, provided with a passage 77 extending the conduit 70 and the bore 71 of the end member 72, is clamped between the body 74 and the end member 72 and a needle valve member 78 regulates the outlet orifice of this ring for putting the passageway 77 and the cavity 60 in communication with conduits 80 provided radially in the body 74 or, on the contrary, preventing any outlet of fluid to the exterior. The combination of the control of the syringe and that of the bleeding needle valve member 78 thus permits the filling of the tube of the catheter, maintaining it full with safety the required time, inflating and deflating the balloon whenever necessary and thereafter emptying the catheter directly through the central cavity 60 and then the conduits 70, 71, 78 and 80. Preferably, in at least one of the distributing elements 48, the central cavity 60 is formed by a central bore which is perpendicular to the conduits 59, 62 and 70 and has a large diameter relative to the diameters of these conduits. A pin 82 is mounted in this bore and is extended at each of the ends thereof by a screwthreaded rod 84 which extends outside the distributing element 48 and on which there are screwthreadedly engaged caps 86 which clamp the sealing washers 88 (FIG. 6).

Withdrawal of the caps 88 and the pin 82 permits an easy cleaning of the distributing element and a re-assembly thereof as often as required. Likewise, the end members 52, 64 and 72, the different parts of the supply head and of the device may be easily unscrewed, cleaned, and possibly sterilized in an oven, and then put back in position after each use. Such facility is very important since the apparatus is intended for delicate treatments and it is most particularly appreciated in respect of the distributing element 48 associated with the silicone syringe 44 owing to the rapidity with which this product solidifies and very rapidly obturates the very small conduits of the distributing element.

Clamps 91 disposed parallel to the clamps 41 and mounted on the same support rod 89 clamp around the micrometer screws 46 which bear against the heads 43, 45 of the pistons of the syringes 42 and 44 and control a precise and progressive filling of the tubes 1 and 2 of the catheter (FIG. 1).

The support 40 also carries through adjustable and inclinable arms 93, 95 at a level higher than that of the syringes 42 and 44, one or more supply syringes supplying other treating products. In the illustrated embodiment, the apparatus has two other syringes, respectively 90 and 92, which supply product, by way of distributing elements 94 and 96 of the same type as the distributing elements 48 (of which the element 94 is associated with a cock 98) to two flexible tubes 99 and 100. The products contained in the syringes 90 and 92 having travelled through the pipes 99 and 100 are mixed inside a distributing head 102 which has, extending therethrough, the tubes of the catheter which are integral with each other, a gland 108 ensuring the fluidtightness of the connection between the head 102 and the catheter extending through the needle 106 and thereby avoiding a flow in return, that is to say a haemorrhage.

At the outlet of the head 102, the catheter passes axially in a tube 104 and enters a hypodermic needle 106 whereby it is possible to introduce it in the veine of the patient. The products coming from the tubes 99 and 100 are also guided by the tube 104 in which they flow around the catheter to the needle 106 and the vessel of the patient. These products, the number and nature of which vary according to the treatments carried out, may thus be employed before or after the catheter, or even simultaneously therewith, owing to a selective actuation of the cocks and bleeding valves.

The driving of the balloon and catheter in the vessel is generally facilitated by the blood itself or by special injections, but it is always necessary to supervise this displacement and to control and even assist it.

It will be understood that the number of syringes 42 and 44 and the number of tubes of the catheter may vary according to the treatment or the examination to be carried out, it being possible to mount each tube on the distributing element of a syringe through a removable socket 18. Whatever be this number, the operations may be carried out rapidly and extremely reliably with a minimum of handling and a maximum of safety. The balloon is solidly secured to the catheter and can only be detached therefrom voluntarily. On the other hand, it may be inflated and deflated whenever desired and thus ensure possibly an injection or a suction. Moreover, the release of the obturating product can be effected without use of an additional means outside the catheter and the balloon may be detached by the action of a diluting fluid, ultrasounds, an electric resistance or an exterior tube sliding on the catheter, or by any other like means with no additional fatigue for the vessels of the patient.

Thus there are provided a catheter and an apparatus which are particularly adapted for neuroradiological examinations and the treatment of blood vessels which permit achieving at last the superselective arteriography of the branches of the internal carotide and the treatment by embolization of aneurysms and cerebral arterioveinous aneurysms. They are also adapted for the angiography and the chemotherapy of tumeurs of the ancephalon, the measurement of the circulatory flow in the arterial branches of small sizes, the superselective injection of fibrinolytic substances up to contact of a clot, and other treatments.

Having now described my invention what I claim as new and desire to secure by Letters Patent is:

1. A catheter structure for the examination or treatment of a blood vessel, comprising inflatable balloon means entirely flexible and of expansible material, at least two flexible capillary tubes which have a uniform diameter and open at one end thereof into the inflatable balloon means, means permanently fixing said one ends of the tubes to the balloon means so that only destruction of a part of the catheter structure would permit separation of the tubes from the balloon means, connecting means mounted on ends of the tubes opposed to said one ends, and means for fixing the connecting means to the tubes in a sealed manner.

2. A catheter structure as claimed in claim 1, wherein the balloon means comprise a balloon and the tubes are parallel and interconnected at said one ends thereof and are independent at said opposite ends thereof.

3. A catheter structure as claimed in claim 1, wherein the tubes are moulded in a single piece.

4. A catheter structure as claimed in claim 1, wherein the balloon means comprise a balloon and the tubes all open into said balloon which is fixed to ends of the tubes which ends are integral with each other.

5. A catheter structure as claimed in claim 1, comprising a removable filament which extends axially through one of the tubes so that when the filament is removed, a free axial passage is formed for a product for separating the balloon means from the tubes.

6. A catheter structure as claimed in claim 1, comprising a destructible filament which extends axially through one of the tubes.

7. A catheter structure as claimed in claim 1, wherein the balloon means comprise a balloon and a diaphragm inside the balloon forms a check-valve preventing a return toward one of the tubes.

8. A catheter structure as claimed in claim 1, wherein the balloon means comprise an individual balloon for each of the tubes which tubes open into their respective balloon, one of the balloons being provided with a calibrated outlet orifice and the other balloon having the tube relating to said one balloon extending therethrough.

9. A catheter structure as claimed in claim 1, wherein the tubes are secured to each other in a part of the length thereof.

10. A catheter structure as claimed in claim 1, wherein the tubes comprise an outer tube and an inner tube disposed one inside the other, the end connecting means of the outer tube having a conduit for the passage of the inner tube which extends therethrough.

11. A catheter structure as claimed in claim 1, wherein one of the tubes has a flared end portion and said connecting means comprise a connecting socket and an end member mounted on said one of the tubes a fixing washer mounted on said one of the tubes between the flared end portion of the tube and the connecting socket.

12. A catheter structure as claimed in claim 10, comprising, inside the connecting means, an elastically yieldable means for closing the outer tube.

13. A catheter structure as claimed in claim 10, wherein the connecting means has means for connection to at least one source of fluid.

14. An apparatus for obturating a blood vessel comprising in combination:
a catheter comprising an inflatable balloon of expansible material, at least one flexible capillary tube having a uniform diameter which opens at one end thereof into the inflatable balloon, an end member mounted on the tube, an outer connecting socket, and means for clamping an end of the tube opposed to said one end in a sealed manner between the end member and the outer connecting socket, a hypodermic needle for the insertion of the catheter in the blood vessel,
a head receiving said connecting socket which socket is removable from the head,
at least two syringes disposed in parallel relation, one syringe for supplying a fluid product and the other for supplying a rapidly solidifiable viscous product, each of the syringes communicating with the head, means for clamping the socket in the head in a sealed manner and for evacuating the space therebetween.

15. An apparatus as claimed in claim 14, wherein the removable socket is mounted with clearance in the head, an annular sealing element is placed between the end of the socket and said head, and adjustable clamping means maintains the socket against the head and compresses the sealing element, it being possible to provide a passage for the evacuation of air urged back between the head and the socket by releasing the clamping means.

16. An apparatus as claimed in claim 14, wherein each syringe has a piston and a micrometer screw is associated with the piston of each syringe for controlling the piston.

17. An apparatus as claimed in claim 14, wherein a distributing element connects the head to the syringe.

18. An apparatus as claimed in claim 17, wherein a bleeding system is mounted on the distributing element of each syringe for fluid product and communicates with the head receiving the corresponding tube of the catheter.

19. An apparatus as claimed in claim 17, wherein the distributing element is provided with an axial bore for cleaning and passageways for communication with the syringe and the connecting socket, the bore having a large diameter and being perpendicular to the passageways, and removable means closing said bore.

20. An apparatus as claimed in claim 14, comprising between the needle and the socket receiving head a mixing and distributing head for mixing treating products and guiding the catheter and said products towards the hypodermic needle.

* * * * *